(12) United States Patent
Pfeifer et al.

(10) Patent No.: US 7,838,823 B1
(45) Date of Patent: Nov. 23, 2010

(54) ION MOBILITY SPECTROMETER WITH VIRTUAL APERTURE GRID

(75) Inventors: Kent B. Pfeifer, Los Lunas, NM (US); Arthur N. Rumpf, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 225 days.

(21) Appl. No.: 12/336,270

(22) Filed: Dec. 16, 2008

(51) Int. Cl.
*H01J 49/00* (2006.01)
(52) U.S. Cl. ...................................... 250/286; 250/281
(58) Field of Classification Search ................. 250/286, 250/287, 281
See application file for complete search history.

(56) References Cited

U.S. PATENT DOCUMENTS

| | | | | |
|---|---|---|---|---|
| 6,639,213 | B2 * | 10/2003 | Gillig et al. | 250/286 |
| 7,155,812 | B1 | 1/2007 | Peterson et al. | |
| 7,705,296 | B2 * | 4/2010 | Wu | 250/282 |
| 2008/0121797 | A1 * | 5/2008 | Wu | 250/283 |
| 2008/0250877 | A1 * | 10/2008 | Wu | 73/864.33 |

OTHER PUBLICATIONS

Herbert H. Hill, Jr. et al, "Ion Mobility Spectrometry", Analytical Chemistry, vol. 62, No. 23, 1990, pp. 1201A-1208A.
Laura M. Matz et al, "Evaluation of suspected interferents for TNT detection by ion mobility spectrometry", Talanta, vol. 54, (2001) pp. 171-179.
Kent B. Pfeifer et al, "Measurement of Ion Swarm Distribution Functions in Miniature Low-Temperature Co-Fired Ceramic Ion Mobility Spectrometer Drift Tubes", Analytical Chemistry, vol. 77, No. 16, 2005, pp. 5215-5220.
Kent B. Pfeifer, et al "Development of Rolled Miniature Drift Tubes Using Low Temperature Co-Fired Ceramics (LTCC)," 13th International Conference on Ion Mobility Spectrometry, Gatlinburg, TN 2004.
Spangler, et al, "Peak Shape Analysis and Plate Theory for Plasma Chromatography", Analytical Chemistry vol. 47, No. 3 (1975) pp. 403-407.
Mahmoud Tabrizchi et al, "A novel electron source for negative ion mobility spectrometry", International Journal of Mass Spectrometry, vol. 218, (2002) pp. 75-85.
Ching Wu, et al, "Construction and characterization of a high-flow, high-resolution ion mobility spectrometer for detection of explosives after personnel portal sampling", Talanta, vol. 57, (2002) pp. 123-134.

* cited by examiner

*Primary Examiner*—Keit T Nguyen
(74) *Attorney, Agent, or Firm*—Kevin W. Bieg

(57) ABSTRACT

An ion mobility spectrometer does not require a physical aperture grid to prevent premature ion detector response. The last electrodes adjacent to the ion collector (typically the last four or five) have an electrode pitch that is less than the width of the ion swarm and each of the adjacent electrodes is connected to a source of free charge, thereby providing a virtual aperture grid at the end of the drift region that shields the ion collector from the mirror current of the approaching ion swarm. The virtual aperture grid is less complex in assembly and function and is less sensitive to vibrations than the physical aperture grid.

10 Claims, 7 Drawing Sheets

ION MOBILITY SPECTROMETER WITH VIRTUAL APERTURE GRID

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to ion mobility spectroscopy and, in particular, to an ion mobility spectrometer with a virtual aperture grid that eliminates the need for a physical aperture grid to prevent premature ion detector response.

BACKGROUND OF THE INVENTION

Ion mobility spectroscopy (IMS), sometimes known as plasma chromatography, is a technology that is ideally suited for the detection of very low levels of analyte due to its extreme sensitivity and ability to speciate. IMS is widely used to detect narcotics, explosives, and chemical warfare agents, since the technique can be tailored to be particularly sensitive to compounds that form negative ions, such as nitrate-laden explosives. Further, because IMS can operate at atmospheric pressure and can detect trace quantities of explosives, it is an attractive technology for use in a miniaturized explosives sensor. See L. M. Matz et al., *Talanta* 54, 171 (2001); C. Wu et al., *Talanta* 57, 123 (2002); M. Tabrizchi et al., *Int. J. Mass Spectrom.* 218, 75 (2002); and K. Cottingham, *Anal. Chem.* 75, 435A (2003).

Ion mobility spectroscopy is based on the atmospheric pressure ionization of a sample vapor and the subsequent separation of the individual ionized components of the sample mixture via electrophoresis as they are accelerated by an external electric field gradient and transit a time-of-flight drift tube against a neutral, counter-flowing gas stream. See G. A. Eiceman and Z. Karpas, *Ion Mobility Spectrometry*, $2^{nd}$ Ed., Chapter 4, CRC Press, Boca Raton, Fla., (2004).

FIG. 1 shows a schematic illustration of a conventional ion mobility spectrometer 10. The sample vapor 12 is drawn into an IMS drift tube 21 and ionized in an ionization region 22 (e.g., using a radioactive source, photoionization, or corona discharge ionizer 23), typically through proton transfer or electron capture reactions with reactant ions, to form product ions. The direction of travel of the ions depends on the polarity of the electric field 24. For example, common explosives contain electronegative nitro functional groups. Therefore, the ionization chemistry for explosives tends to form negative ions. Halogenated compounds, such as methylene chloride, can be added to a carrier gas in the ionization region 22 to provide chloride reactant ions (i.e., $Cl^-$). The chloride reactant ions can then transfer charge to the electronegative explosive molecules to form molecular ions.

A gate drive circuit 25 provides a trigger to a gate 26, thereby providing an ion pulse 14 that is gated into a drift region 15 to begin a new measurement cycle. IMS drift tubes have normally been operated by opening an electrostatic ion shutter to allow a narrow pulse of ions into the time-of-flight drift region where they move toward an ion collector 27 as a single ion swarm to be measured as a transient collected current. The gate can be an electrostatic ion shutter, such as a Bradbury-Neilson or Tyndall type shutter. With a Bradbury-Neilson shutter, a transverse electric field is applied to drive the ions into a perpendicular trajectory from the axis into a conductor where ion annihilation occurs resulting in a cutoff of ion flow in the drift tube. The related Tyndall shutter uses two closely spaced planes of electrodes consisting of parallel wires or screens. A voltage is applied or removed between the planes to annihilate the ions during an off cycle and then release them into the drift tube as a pulse of ions. Conventional gating techniques, such as Tyndall and Bradbury-Neilson gates, operate more like camera shutters and do not compress the ions as a result of an accumulation cycle. Another type of gate uses a single potential plane to form a potential well in the drift tube. This gate provides a potential capture well that controls the injection of ions into the drift region by first collecting the ions and then releasing them as a pulse.

Drift gas is injected into the drift tube 21 via a drift gas inlet 17 and removed through a drift gas outlet 18. In the drift region 15, the ions establish a terminal velocity under the influence of the potential gradient of the electric field 24 and are separated into single ion swarms according to their characteristic ion mobility against the counter-flowing drift gas 16. The separation begins at the entrance gate 26 and terminates at the ion collector 27 at the end of the drift region 15, where the ion response signal is recorded. For example, the ion collector 27 can comprise a collecting electrode or Faraday plate that records an ion response current. The response of the IMS drift tube 21 is measured as a function of ion current versus the ion arrival time at the ion collector 27 for a measurement cycle. Typically, the ion detector comprises an operational amplifier 28 for converting the ion response current into an ion mobility spectrum. The spectrum of ion arrival times at the ion collector indicates the relative ion mobility of each ion through the drift region. Compound identification is typically based on the comparison of the ion mobility spectrum generated from the sample with the spectrum of a known standard.

The resolution of the IMS is related to the drift time divided by the pulse width at the one-half amplitude of a single ion swarm. The pulse width is subject to several broadening mechanisms including the initial gated pulse width, diffusional broadening, electrostatic space charge repulsion, electric field gradients, temperature gradients, gate depletion/dynamic leakage, pressure fluctuations, ion molecule reactions in the drift space, and capacitive coupling between approaching ions and the ion collector. See R. H. St. Louis and H. H. Hill, *Anal. Chem.* 21, 321 (1990). In particular, capacitive coupling between an approaching ion swarm and the ion collector causes an asymmetry in the rising edge of the response current. Therefore, a physical aperture grid 29, constructed from an array of small wires suspended across the interior of the drift tube, is located just ahead of the ion collector 27 to capacitively decouple the approaching ion cloud and prevent peak broadening due to a premature detector response. However, the addition of an aperture grid to the spectrometer results in increased complexity of the system in both assembly and function. In addition, it leads to a large source of noise in the spectrometer as the grid can be vibration sensitive and generate an additional current that is a function of acoustic vibration in the environment.

Therefore, a need remains for an ion mobility spectrometer that does not require a physical aperture grid to eliminate capacitive coupling of an ion swarm to the ion collector.

SUMMARY OF THE INVENTION

The present invention is directed to an ion mobility spectrometer, comprising an ionizing region for ionizing a sample vapor to form ions, a drift tube comprising a drift region in which the ions drift under the influence of an electric field, established by a plurality of stacked electrodes, against a counter-flowing drift gas and are separated into at least one single ion swarm therein, a gate for pulsing the ions into the drift region, an ion collector for detecting the single ion swarm at the end of the drift region to provide an ion mobility spectrum, and wherein at least two of the stacked electrodes adjacent to the ion collector have an electrode pitch that is less than the width of an ion swarm and each of the adjacent electrodes is connected to a source of free charge, thereby providing a virtual aperture grid at the end of the drift region that shields the ion collector from the mirror current of the ion swarm. The source of free charge can be a low-pass electrical circuit that has a cut-off frequency below a minimum frequency component of the ion swarm. The number of electrodes in the virtual aperture can typically be four of five. The electrode pitch can typically be less than 5 mm and more typically less than 0.75 mm.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

DETAILED DESCRIPTION OF THE INVENTION

Ion mobility spectrometer drift tubes have been traditionally constructed to have a constant radius, cylindrical structure with a constant axial electric field to transport the ions from the ion source to the detector. Ions are produced in the ionization region and transported, via the electric field, to the gate. An ion pulse is released by the gate and travels through the drift tube and separated ions are detected with a Faraday plate positioned at the end of the drift tube.

Figure 2:
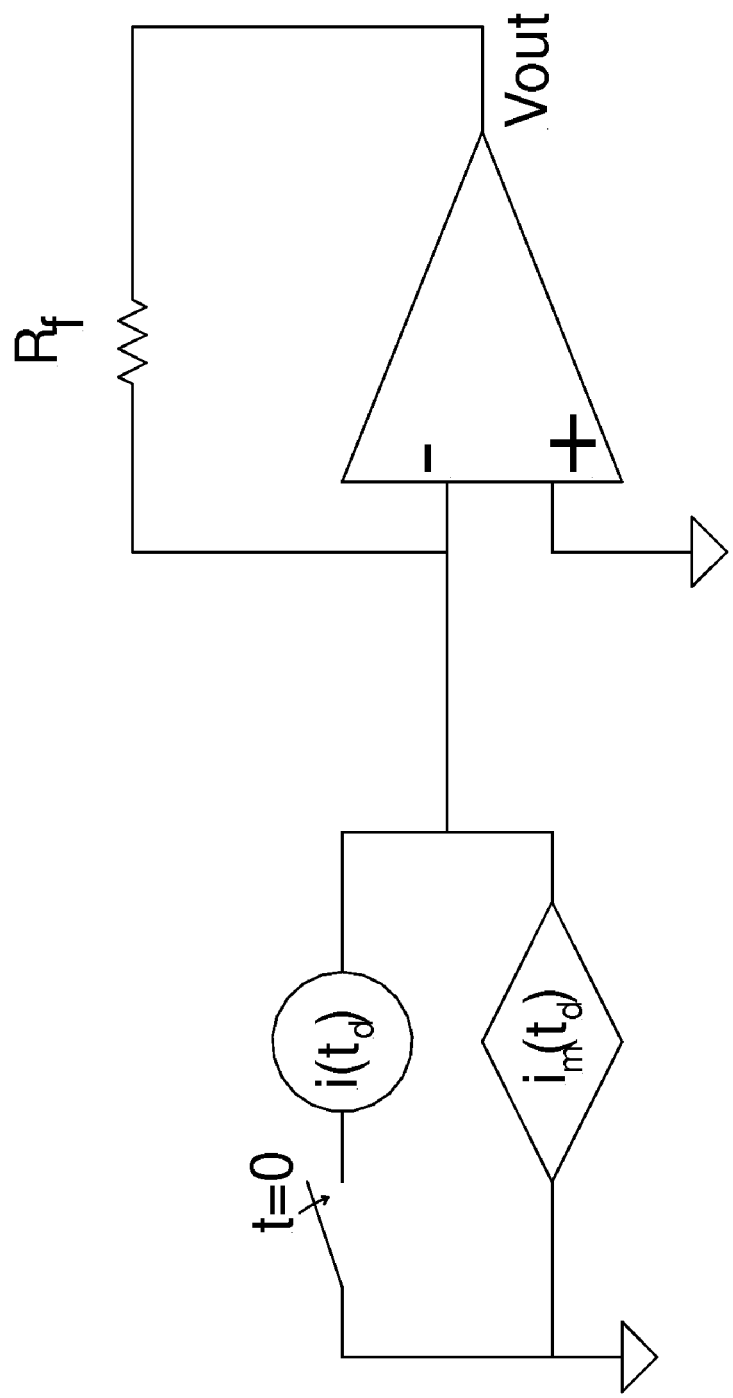
FIG. 2 is a schematic diagram of an electronic model of an IMS detector illustrating the amplifier and the effective current of the drift tube and the dependent mirror current.

Detection occurs as the ions collide with the Faraday plate. As a result, charges are drawn from the electronic detection circuit and a current occurs. The current is generally amplified via a "trans-impedance" operational amplifier into a voltage that is proportional to the ion current. A circuit model of the IMS tube and the first stage of amplification is shown in FIG. 2. The current collected at the Faraday plate is given as $i(t_d)$, the drift time is denoted as $t_d$, and the dependent "mirror" current is given as the dependent current source $i_m(t_d)$. Assuming that the operational amplifier is ideal in that the input impedance is infinite, the expression for the output voltage of the amplifier can be written as:

$$V_{out} = R_f(i(t_d) + i_m(t_d)) \quad [1]$$

In the literature, it has been shown that the general charge density of an ion swarm in drift tubes, where the tube diameter is large compared to the ion swarm diameter and the electric field is constant, is of the following general form in cylindrical coordinates:

$$\rho(z, r) = \rho_o e^{-((\frac{z}{a})^2 + (\frac{r}{w})^2)} \quad [2]$$

where $\rho(z,r)$ is the charge density as a function of radius (r) and axial direction (z), $\rho_o$ is the initial charge density, w is the 1/e radius, and a is the 1/e width along the z-axis. See E. M. Mason and E. W. McDaniel, *Transport Properties of Ions in Gases*, John Wiley and Sons, New York, pp 85-89 (1988); G. E. Spangler and C. I. Collins, *Anal. Chem.* 47, 403 (1975); and K. B. Pfeifer and A. N. Rumpf, *Anal. Chem.* 77(16), 5215 (2005). Eq. [2] is simply a Gaussian in the axial direction multiplied by a Gaussian in the radial direction with a scale factor that is set by the initial conditions. By the method of images, an equation for the surface charge density on the Faraday plate ($\sigma(r)$) as a function of radial position is given by:

$$\sigma(r) = \frac{z\rho_o}{2\pi} \int_0^{2\pi} d\phi \int_0^r \int_{z_o}^z \frac{e^{-((\frac{z}{a})^2 + (\frac{r}{w})^2)}}{(z^2 + r^2)^{\frac{3}{2}}} r \, dr \, dz \quad [3]$$

where $z_o$ is the average distance of the ion swarm from the Faraday plate and $\phi$ is the cylindrical angle. See J. R. Reitz et al., *Foundation of Electromagnetic Theory*, Addison-Wesley, Reading, M A, pg. 63-64 (1980).

Since, in general, a<w and assuming that a is roughly constant, the ion swarm can be approximated as a sheet of charge and Eq. [3] can be simplified as:

$$\sigma(r, t) \cong -z\rho_o \Delta z \int_0^r \frac{r \, dr}{(z(t)^2 + r^2)^{\frac{3}{2}}} \quad [4]$$

$$\sigma(r, t) \cong -\rho_o \Delta z \left[1 - \frac{z(t)}{(r^2 + z(t)^2)^{\frac{1}{2}}}\right]$$

Since $\sigma(r)$ is a function of the radial position of the induced charge on the Faraday plate, it is also a function of time since the axial position of the swarm is a function of time. Thus, the total charge on the Faraday plate can be determined as a function of time by integrating Eq. [4] over the surface of the Faraday plate:

$$q(t) = \int \sigma(r, t) dA = -\rho_o \Delta z \int_0^{2\pi} d\phi \int_0^R \left(r - \frac{zr}{(r^2 + z^2)^{\frac{1}{2}}}\right) dr \quad [5]$$

-continued $$q(t) = -2\pi\rho_o \Delta z \left[ \frac{R^2}{z} - z(R^2 + z^2)^{\frac{1}{2}} + z^2 \right]$$

By taking the derivative with respect to time of Eq. [5] and combining it with the equation for the ion drift position in an IMS (z=L−xEt), an expression for the mirror current at the Faraday plate can be written as:

$$i_m(t) = -2\pi\rho_o \Delta z \kappa E_o \left[ \frac{R^2 + 2(L - \kappa E_o t)^2 +}{2(L - \kappa E_o t)((\kappa E_o t)^2 - 2L\kappa E_o t + L^2)^{\frac{1}{2}}} \right] \quad [6]$$

where L is the length of the drift region of the tube, κ is the mobility of the ion, and $E_o$ is the electric field in the tube.

Figure 3:
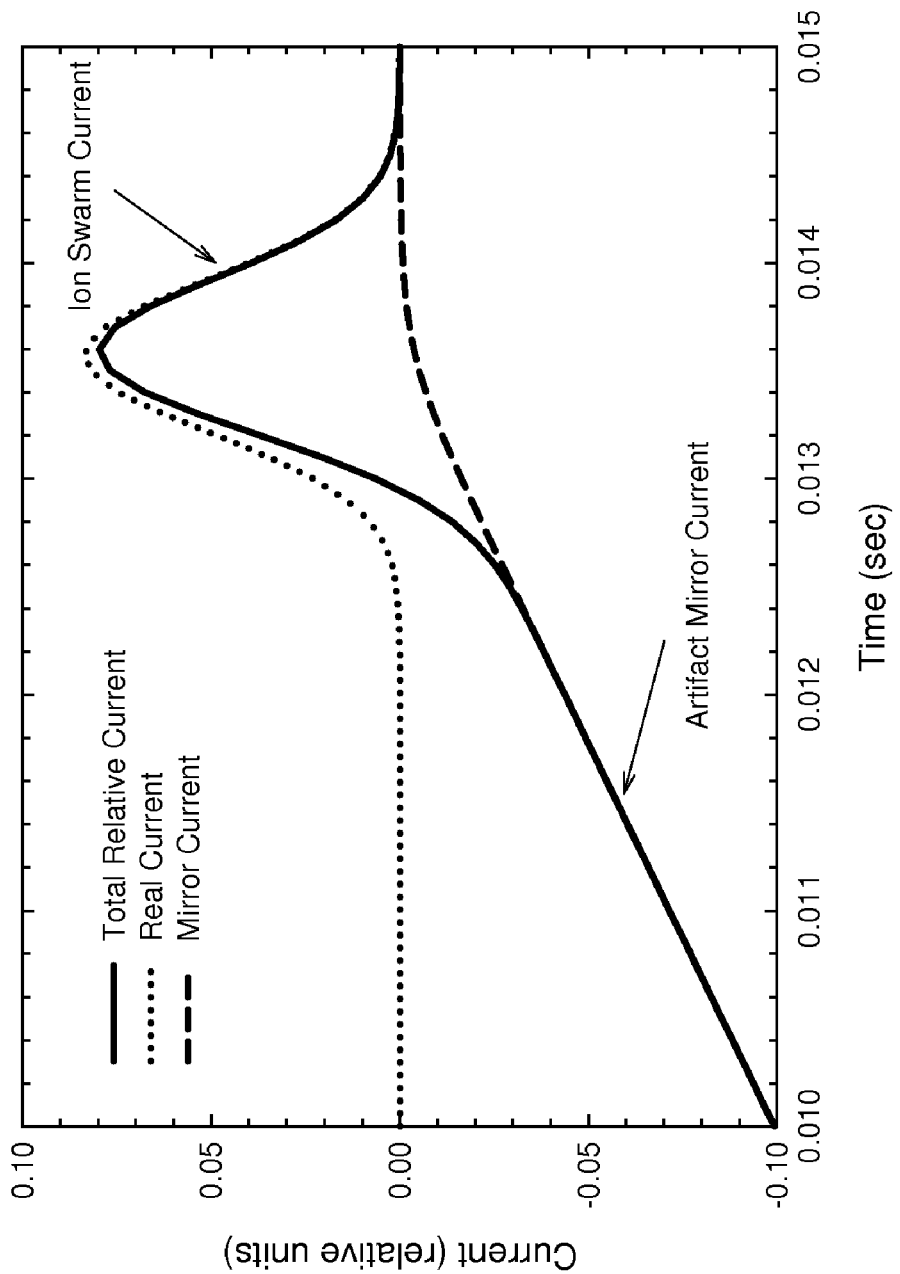
FIG. 3 is a plot of real current (dotted line), mirror current (dashed line), and total current (solid line) for an IMS with no aperture grid. There is a linear increase in the mirror current prior to arrival of a Gaussian real current pulse.

FIG. 3 shows a plot of the real current, mirror current, and total current for a conventional IMS without an aperture grid. The solid line represents the total current observed by the operational amplifier during the arrival of the ion swarm. The linearly increasing baseline is due to the mirror current (dashed line) observed as the surface charge density increases as a function of position as the ion swarm approaches the Faraday plate. This mirror current is an artifact of the finite extent of the Faraday plate. If the Faraday plate were much larger than the charge distribution, then while the charges would move in the plate, the total charge would remain constant resulting in no mirror current contribution. The real current is shown as a dotted line.

Figure 1:
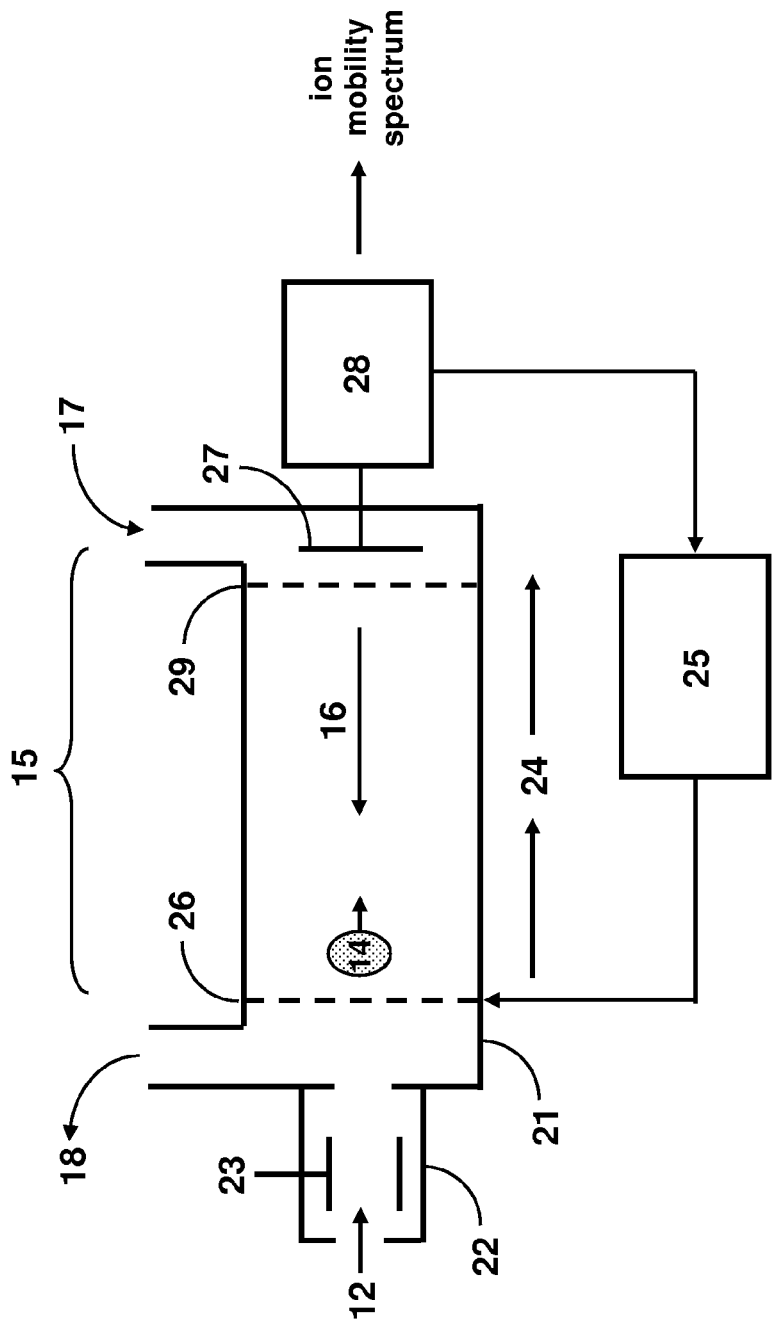
FIG. 1 is a schematic illustration of a conventional ion mobility spectrometer comprising an aperture grid to capacitively decouple an approaching ion swarm from the ion collector.

As shown in FIG. 1, in a conventional ion mobility spectrometer, this mirror current contribution is substantially eliminated by placing a physical aperture grid in front of the Faraday plate. This aperture grid typically consists of a grid of conductors placed perpendicular to the axis that constitutes an equipotential surface off of which is formed the mirror element rather than off of the Faraday plate. This eliminates the mirror current effect in the ion mobility spectrum by sourcing the mirror charge from the aperture grid power supply rather than the detection electronics. However, the addition of an aperture grid to the IMS results in increased complexity of the system in both assembly and function. In addition, it leads to a large source of noise in the IMS as the grid can be vibration sensitive and generate an additional current that is a function of acoustic vibration in the environment.

Figure 4:
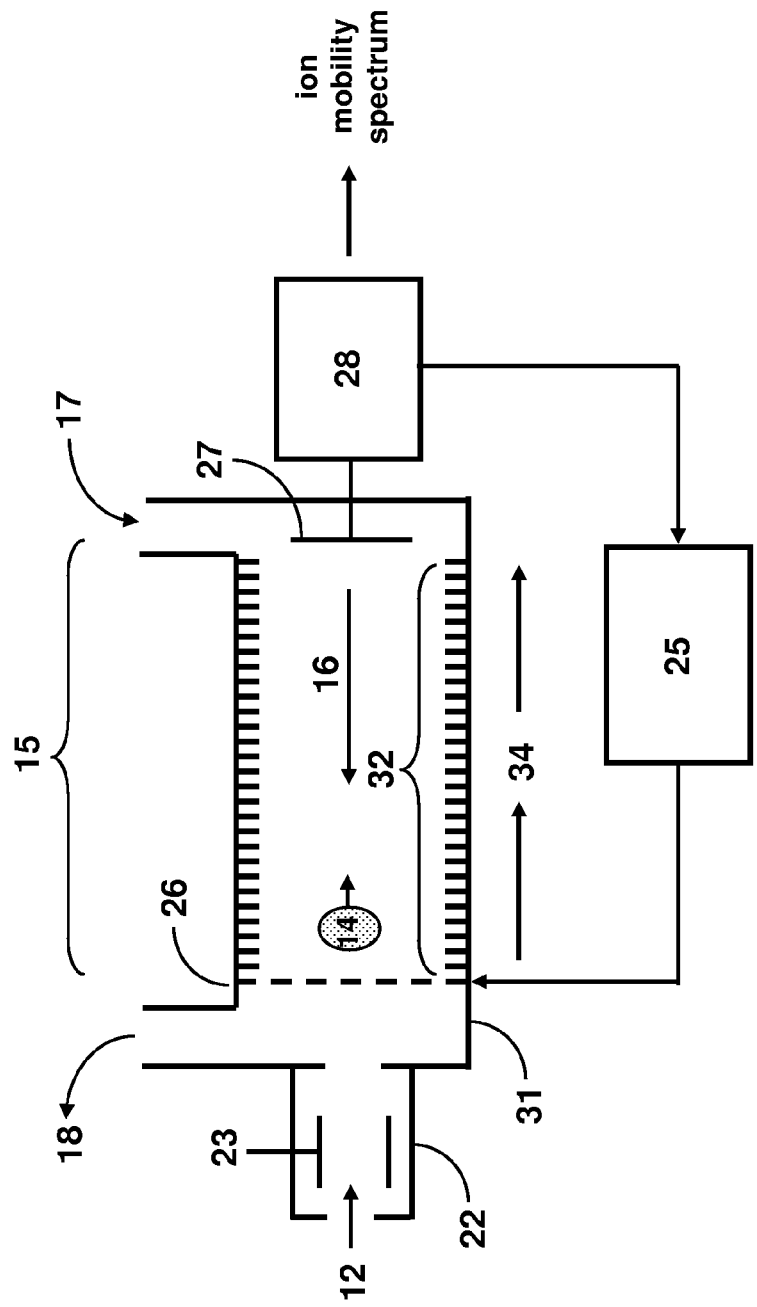
FIG. 4 is a schematic illustration of an ion mobility spectrometer with a virtual aperture grid.

The present invention is directed to an ion mobility spectrometer that requires no physical aperture grid (i.e., it uses a virtual aperture grid), resulting in the reduced system complexity and reduced noise. FIG. 4 shows a schematic illustration of an ion mobility spectrometer 30 with no physical aperture. As with the conventional ion mobility spectrometer 10, the sample vapor 12 is drawn into an IMS drift tube 31 and ionized in an ionization region 22 by an ionizer 23. A pulse of ions 14 is periodically gated into the drift region 15 of the drift tube 31 by a gate 26. The drift tube 31 further comprises a series of stacked electrodes 32 to provide a uniform electric field 34 in the drift region 15. In the drift region, the ions establish a terminal velocity under the influence of the potential gradient of the electric field 34 and are separated into single ion swarms according to their characteristic ion mobility against the counter-flowing drift gas 16. The separation begins at the entrance gate 26 and terminates at an ion collector 27 at the end of the drift region 15, where the ion response signal is recorded. For example, the ion collector 27 can be a Faraday plate that records an ion response current. The ion response current can be amplified via an operational amplifier 28 into a voltage that is proportional to the ion current, thereby providing an ion mobility spectrum.

To maintain resolution in a drift tube, it is important that the local electric field be a constant over as much of the cylindrical cross section as possible. Since electric field is a vector quantity, this requires that the direction be parallel with the axis and the magnitude be constant. Uniform electric fields provide every ion with an equal probability of transport via electric forces to the ion collector at exactly the same drift velocity, independent of its initial conditions. If an ion is transported to the collector in a region of non-uniform field, such as very near the tube walls, its path will be substantially longer than an ion transported down the center of the drift tube. This results in temporal dispersion of the ion swarm and associated resolution loss in the tube. Therefore, a high linear density of stacked electrodes is generally used to increase the region of electric field uniformity in a small radius drift tube. Providing numerous closely spaced electrodes limits regions of electrical non-uniformity and improves the resolution of the IMS.

Figure 5:
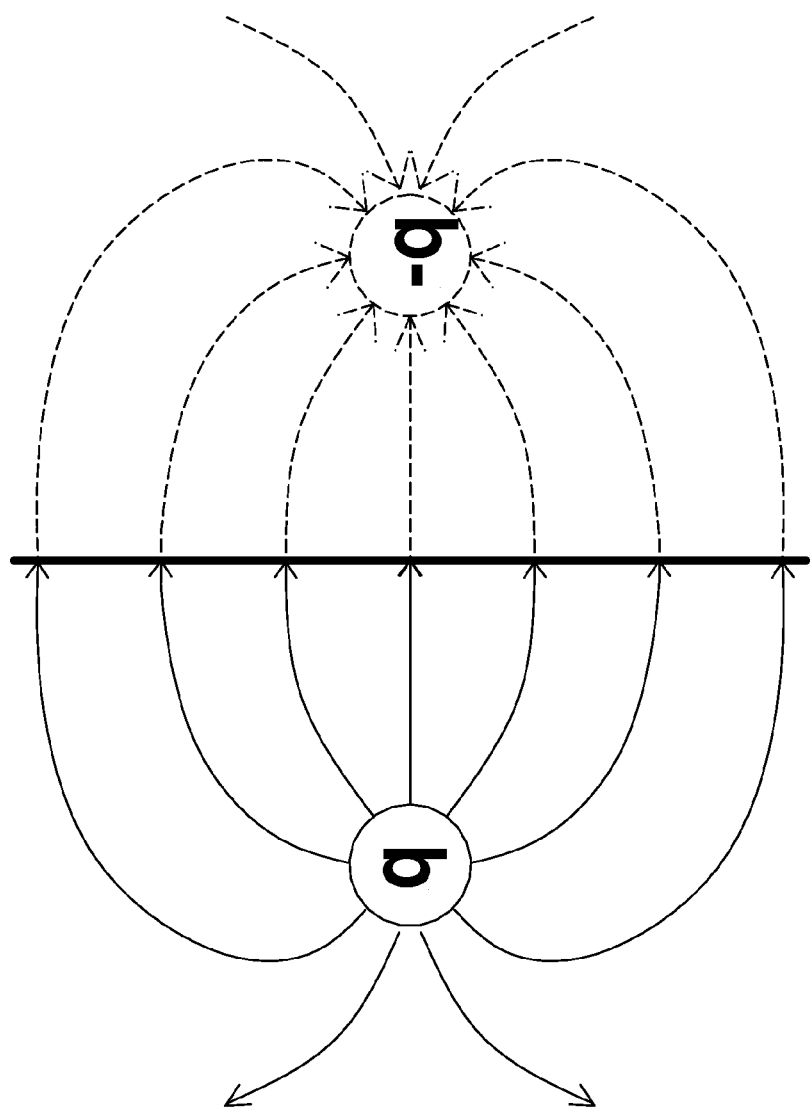
FIG. 5 is a diagram of image charge compared to charge on an equipotential surface. The charge on the left is a real charge that terminates on the equipotential surface. The mirror charge on the right hand side is a mathematical construct that allows the boundary condition at the equipotential surface to be met.

FIG. 5 is a diagram of image charge compared to charge on an equipotential surface. The charge on the left is a real charge that terminates on the equipotential surface. The mirror charge on the right hand side is a mathematical construct that allows the boundary condition at the equipotential surface to be met. The theory for mirror charges that leads to the mirror current of Eq. [6] indicates that the image charge is a virtual image (right hand charge in FIG. 5) that does not actually exist in the tube but only in the form of the charges redistributed on the equipotential surface. Thus, if a source of charge, such as a battery or capacitor, works to maintain the equipotential surface, free charge is available to move such that the effect of real charge is screened from the right hand side of the picture.

By placing several stacked electrodes very close together such that their spacing is much less than the spatial extent of the charge swarm and giving each of them an individual source of charge, such as a capacitor, screening of the moving swarm can be accomplished until the ion swarm is within a single electrode spacing of the Faraday plate. As an example, if the spacing of the control grids is 0.75 mm, the initial width of a swarm is impliedly never narrower than 0.75 mm. For a typical ion swarm drifting in an IMS, the speed is on the order of 5 m/s and the temporal width of the gate pulse is on the order of 0.5 to 1 ms in width. Thus, the physical width of an ion swarm is typically on the order of 2-5 mm. If the IMS tube uses a very narrow pitch for the electrodes that is smaller than the width of the ion swarm, then it is possible to construct a "virtual" aperture grid that shields the Faraday plate from the changing mirror current while avoiding the added complexity and sensitivity to noise that is inherent in a physical aperture grid.

Figure 6:
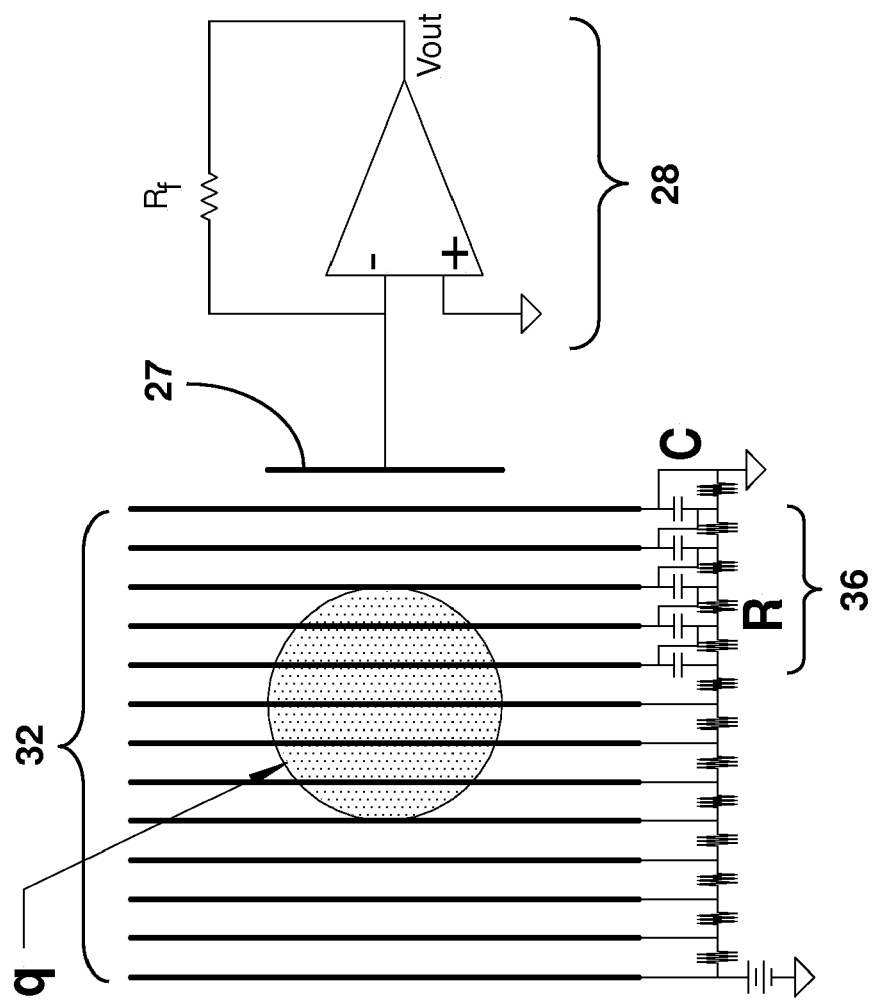
FIG. 6 is a schematic illustration of an implementation of a virtual aperture grid in an IMS.

FIG. 6 is a schematic illustration of an implementation of a virtual aperture grid in an ion mobility spectrometer 30. Vertical lines are the stacked electrodes 32 of the IMS drift tube 31 with a hole in the center for ions to pass through. In this example, the last five electrodes 36 adjacent to the ion collector 27 are instrumented with capacitors as a source of free charge to keep the potential of the electrodes planar and the voltage difference between the electrodes constant, therefore providing a virtual aperture grid at the end of the tube. The virtual aperture grid acts as a screening field for the moving charge and, as a consequence, produces no mirror charge in the Faraday plate of the ion mobility spectrometer. In this example, all of the values of R and C can be the same.

The spacing of the electrodes and the values of the capacitors are determined by the geometry of the gate and initial ion pulse width, the desired electric field in the tube (E), the effects of diffusion (D), electrostatic repulsion, and other spreading mechanisms in the tube. Coupled with the effects of the other spreading mechanisms, the final ion number density (n), after travel through the tube, can be described by solution of the following non-linear partial differential equation, where z is defined as the tube axial direction:

$$\frac{\partial n}{\partial t} = -\kappa \frac{\partial n}{\partial z}\left(E + \int \frac{q}{\varepsilon_o} n dz'\right) - \frac{\kappa q}{\varepsilon_o} n^2 + D \frac{\partial^2 n}{\partial z^2} \quad [7]$$

Eq. [7] cannot be solved analytically but can be determined numerically to find the width of the final ion swarm at the detector. Preferably, the electrode pitch can be high enough such that the swarm is 4 to 5 times wider than the electrode spacing in the virtual aperture grid. It is reasonable to assume that higher pitches will work even better. A design equation for an m-electrode virtual aperture grid (m is the number of electrodes forming the grid adjacent to the ion collector) with an electrode pitch (P) is given in Eq. [8], where L is the length of the tube and R' is the desired resolution of the tube.

$$P = \frac{L}{mR'} \quad [8]$$

A practical number of m is approximately four to five electrodes.

The value of the capacitance in FIG. 6 is determined by several tube parameters; namely the power supply voltage ($V_{max}$), the minimum mobility that is to be measured ($\kappa_{min}$), and the resistance between tube electrodes (R), as follows:

$$C > \frac{2L^2}{RR'\kappa_{min}V_{max}} \quad [9]$$

Eq. [9] is derived by recognizing that the mirror image charge will distort the shape of the potential gradients at the electrodes nearest the ion collector which will be measured by the electronic detection circuit. By constructing a low-pass network that has a cut-off frequency below any frequency that will appear in the tube due to ion motion in the swarm, the potential of the nearest electrodes adjacent to the ion collector can be forced to remain constant which in-turn forces the potential gradients at those electrodes to remain planar, effectively forming an aperture grid.

Eq. [9] is based on the assumption that the electric field and electrode pitch is constant over the entire length of the IMS tube, as is generally the case. However, a constant electric field is not necessary for an IMS tube design to function. In the case of a non-linear electric field or electrode pitch, the virtual aperture grid can be designed by determining the average electric field magnitude (E) at the virtual aperture grid electrodes and rewriting Eq. [9] as follows:

$$C > \frac{2L}{RR'\kappa_{min}E} \quad [10]$$

To demonstrate a virtual aperture grid, a miniaturized IMS drift tube was constructed that was similar in design to the larger "stacked" drift tubes found in commercial systems. The miniature IMS drift tube was constructed from rolled, low-temperature co-fired ceramics (LTCC) with integral potential resistors. LTCC allows simple screen-printing processing for the production of the stacked electrodes, and on-board surface mount resistors fabricated directly on the tube reduce the number of electrical connections required without sacrificing the performance of numerous electrodes with small spacing. In addition, integral heating elements were incorporated into the structure for operation at elevated temperature. Control structures were constructed using LIGA (LIGA is a German acronym that stands for lithography, electroforming, and molding) processing that were inserted into the tubes and formed the gate structures of the tube. The end pieces containing the gas inlets, target, apertures, and a 20 $\mu Ci^{241}$ Am ionization source were constructed from the LTCC and bonded to the tubes. See K. B. Pfeifer and R. C. Sanchez, *Int. J. Ion Mobility Spectroscopy* 5, 63 (2002); and U.S. Pat. No. 7,155,812 to Peterson et al., which are incorporated herein by reference.

The gate used a potential well to capture ions rather than to block the flow of ions by annihilation as in the case of a Bradbury-Neilsen or a Tyndall gate. To provide the gate, two conducting LIGA formed grid structures spaced 0.75 mm apart were used to provide a uniform potential contour across the diameter of the tube at their respective potentials. The first grid structure was actively switched to provide a 25 V potential energy well in the potential field. The second grid was permanently biased such that it reestablished the uniform electric field found in the rest of the tube and also shielded the detector pin from the field disturbance due to the gate switching. Ions of low kinetic energy are trapped in this potential well, and the charge density becomes locally higher resulting in electrostatic repulsion effects initially spreading the captured ion swarm when the potential well is released. Therefore, the initial width of the ion pulse must be on the order of the spacing between the two LIGA grids (i.e., 0.75 mm), otherwise ions would enter into the drift region and escape the well. See W. C. Blanchard, *Int. J. Mass Spectrom. Ion Processes* 95, 199 (1989).

Methylene chloride ($CH_2Cl_2$) gas was injected into the drift tube by way of a drift gas flow of about 100 sccm room air (10-20% RH, 23° C.) that was first passed over a diffusion tube containing liquid $CH_2Cl_2$. This gave a $CH_2Cl_2$ concentration in the ionization chamber of about 300 ppm.

The LTCC drift tube had a 12-mm-bore and 57-mm-drift length. The tube had a high density of stacked electrodes (80 electrodes) spaced at 0.75-mm center-to-center pitch over the length of the drift tube to maintain a uniform electric field in the center of the tube. A variable high-voltage dc power supply could provide electric fields in the center of the tube that ranged from 0 to 18 kV/m. A signal generator was used to set the overall timing of the circuit connected to a variable-width pulse generator. The output of the pulse generator was used to trigger an oscilloscope and the drive electronics of the IMS circuit board. The IMS circuit board contained the necessary high-voltage supply for the tube potential gradient as well as switching circuitry that allows for development of 5-70 V potential wells in the tube. The highest signal-to-noise ratio occurred with a potential well on the order of 25 V, which was used for this demonstration. The circuit board also contained a 200-dB gain trans-impedance operational amplifier with a nine-pole band-pass filter (10-5500 Hz). The ion current was amplified by the operational amplifier and recorded as an ion mobility spectrum by the oscilloscope.

The value of R in Eq. [9] can generally be determined from the maximum current sourcing capability of the power supply and is preferably large enough such that the tube will not load the supply. For this exemplary tube, the supply voltage was 2000 V with a 0.5 mA maximum current capability (i.e., 1 W). The resistance between the 81 electrodes was 140 kΩ for maximum current of 0.18 mA. The resolution of the 57 mm drift tube was designed to be approximately 15, indicating an electrode pitch from Eq. [8] of 0.75 mm. The capacitance can then be calculated from Eq. [9] assuming a minimum ion mobility of 1 cm$^2$/(Vs). The minimum capacitance that will function as a virtual aperture grid is 15 nF for this tube design. To provide an order of magnitude "buffer" in the low-pass cut-off, the virtual aperture grid in this example used 220 nF capacitors. The capacitance is determined by the RC time constant and can vary depending on the resistor used, tube design, and power supply source capability. Although as few as one electrode can be used, two electrodes is a practical minimum due to finite conductivity and stray capacitance in the system. There is no theoretical limit to the number of electrodes that can be used in the virtual aperture grid, however adding additional electrodes adds more complexity. The number of electrodes that form the virtual aperture grid was four in this exemplary tube. The spacing of the Faraday plate collector from the last electrode in the tube was approximately equal to the electrode pitch of 0.75 mm.

Figure 7:
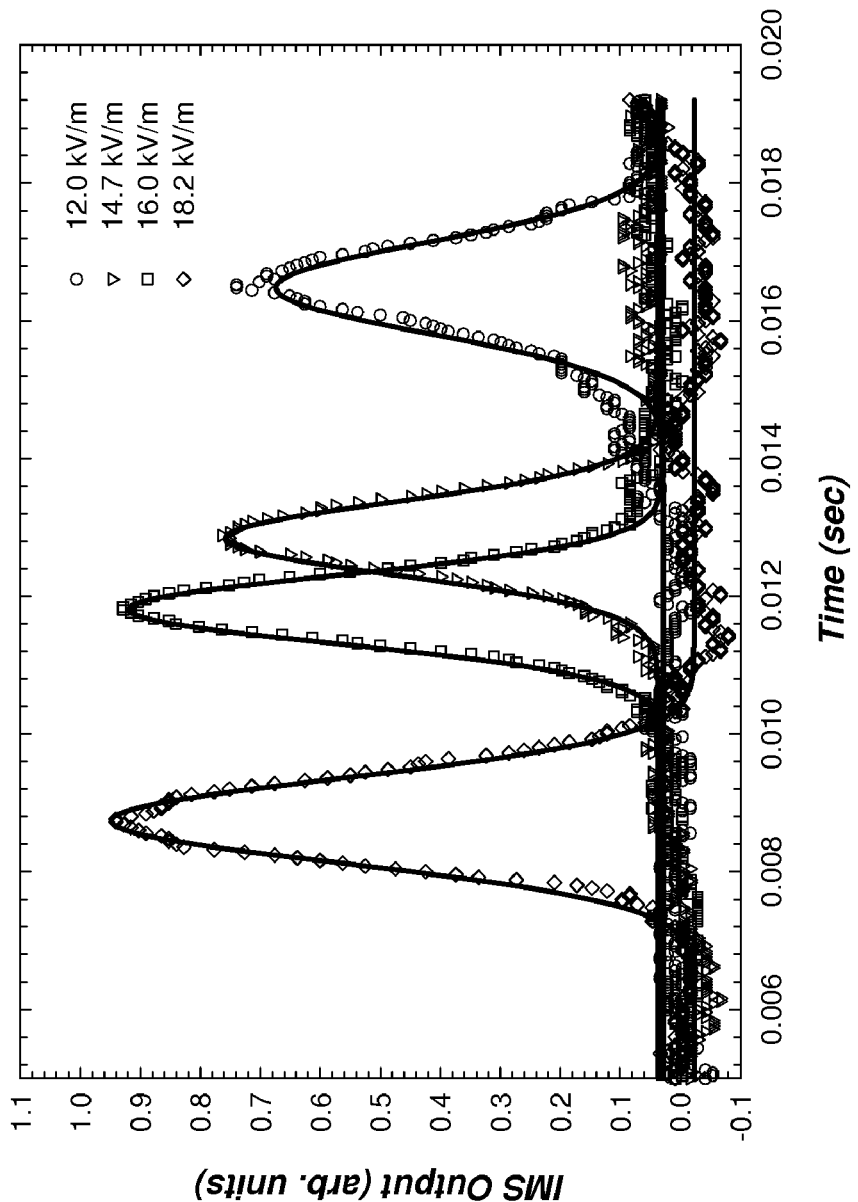
FIG. 7 is plot of IMS response for a 12-mm diameter LTCC drift tube with a virtual aperture grid. This plot is for a Cl⁻ reactive ion peak in the tube with a 500 μs gate time and various field magnitudes from 12-18 kV/m.

FIG. 7 is a plot of ion mobility spectra obtained with the 12-mm drift tube with the virtual aperture grid, as described above. A Cl$^-$ ion pulse was derived from CH$_2$Cl$_2$ at room temperature with a 500-μs gate time. The electric field magnitude in the tube was varied from 16-18 kV/m. Solid lines are fits of the spectra to a current function based on the charge distribution of Eq. [2]. See K. B. Pfeifer and A. N. Rumpf, Anal. Chem. 77(16), 5215 (2005). Capacitive coupling should lead to asymmetry in the pulse on the rising edge. The spectra illustrate that the response is symmetrical over a large range of tube electric field magnitudes. The symmetry illustrates that the current is essentially only from the ion swarm and no mirror current is measured by the Faraday plate. This indicates that the mirror current is essentially eliminated from the measurement validating the function of the virtual aperture grid. Further, the symmetry of the spectra verifies that there is very little temporal dispersion of the ion swarm in the drift tube.

The present invention has been described as an ion mobility spectrometer with a virtual aperture grid. It will be understood that the above description is merely illustrative of the applications of the principles of the present invention, the scope of which is to be determined by the claims viewed in light of the specification. Other variants and modifications of the invention will be apparent to those of skill in the art.

We claim:

1. An ion mobility spectrometer, comprising:
   an ionizing region for ionizing a sample vapor to form ions,
   a drift tube comprising a drift region in which the ions drift under the influence of an electric field, established by a plurality of stacked electrodes, against a counter-flowing drift gas and are separated into at least one single ion swarm therein,
   a gate for pulsing the ions into the drift region,
   an ion collector for detecting the at least one single ion swarm at the end of the drift region to provide an ion mobility spectrum, and
   wherein at least two of the stacked electrodes adjacent to the ion collector have an electrode pitch that less than the width of an ion swarm and each of the adjacent electrodes is connected to a source of free charge, thereby providing a virtual aperture grid at the end of the drift region that shields the ion collector from the mirror current of the ion swarm.

2. The ion mobility spectrometer of claim 1, wherein the source of free charge comprises a low-pass electrical circuit that has a cut-off frequency below a minimum frequency component of the ion swarm.

3. The ion mobility spectrometer of claim 2, wherein the source of free charge comprises a capacitor.

4. The ion mobility spectrometer of claim 3, wherein the capacitor has a capacitance of greater than $$C > \frac{2L^2}{RR'\kappa_{min}V_{max}},$$

where C is the capacitance, L is the length of the drift tube, R is the resistance between the stacked electrodes, R' is the desired resolution of the tube, $\kappa_{min}$ is the minimum mobility of the ions, and $V_{max}$ the power supply voltage on the stacked electrodes.

5. The ion mobility spectrometer of claim 3, wherein the capacitor has a capacitance of greater than $$C > \frac{2L}{RR'\kappa_{min}E},$$

where C is the capacitance, L is the length of the drift tube, R is the resistance between the stacked electrodes, R' is the desired resolution of the tube, $\kappa_{min}$ is the minimum mobility of the ions, and E is the average field strength at the virtual aperture grid electrodes.

6. The ion mobility spectrometer of claim 1, wherein the number of adjacent electrodes is five or less.

7. The ion mobility spectrometer of claim 1, wherein the adjacent electrode pitch is less than $$P = \frac{L}{mR'},$$

where P is the pitch, L is the length of the drift tube, R' is the resolution of the tube, and m is the number of electrodes comprising the virtual aperture grid.

8. The ion mobility spectrometer of claim 7, wherein m is five or less.

9. The ion mobility spectrometer of claim 1, wherein the adjacent electrode pitch is less than 5 mm.

10. The ion mobility spectrometer of claim 1, wherein the adjacent electrode pitch is less than 0.75 mm.

* * * * *